US008257688B2

(12) United States Patent
Friedman et al.

(10) Patent No.: US 8,257,688 B2
(45) Date of Patent: *Sep. 4, 2012

(54) CONTROLLED DELIVERY SYSTEM OF ANTIFUNGAL AND KERATOLYTIC AGENTS FOR LOCAL TREATMENT OF FUNGAL INFECTIONS OF THE NAIL AND SURROUNDING TISSUES

(75) Inventors: Michael Friedman, Jerusalem (IL); Daniella Licht, Givat Shaumel (IL); Avraham Yacobi, Englewood, NJ (US)

(73) Assignee: Taro Pharmaceuticals Industries, Haifa Bay (IL)

( * ) Notice: Subject to any disclaimer, the term of this patent is extended or adjusted under 35 U.S.C. 154(b) by 123 days.

This patent is subject to a terminal disclaimer.

(21) Appl. No.: 12/652,331

(22) Filed: Jan. 5, 2010

(65) Prior Publication Data
US 2010/0160273 A1 Jun. 24, 2010

Related U.S. Application Data

(63) Continuation-in-part of application No. 11/313,186, filed on Dec. 20, 2005, now Pat. No. 7,678,366, which is a continuation of application No. 09/534,960, filed on Mar. 27, 2000, now Pat. No. 7,074,392.

(51) Int. Cl.
*A61K 8/18* (2006.01)
(52) U.S. Cl. ........................................................ 424/61
(58) Field of Classification Search ........................ None
See application file for complete search history.

(56) References Cited

U.S. PATENT DOCUMENTS

| | | | |
|---|---|---|---|
| 4,250,164 A | 2/1981 | Bernstein | |
| 4,402,935 A | 9/1983 | Gordon et al. | |
| 4,957,730 A | 9/1990 | Bohn et al. | |
| 5,023,082 A | 6/1991 | Friedman et al. | |
| 5,120,530 A | 6/1992 | Ferro et al. | |
| 5,160,737 A | 11/1992 | Friedman et al. | |
| 5,264,206 A * | 11/1993 | Bohn et al. | 424/61 |
| 5,346,692 A | 9/1994 | Wohlrab et al. | |
| 5,391,367 A * | 2/1995 | DeVincentis et al. | 424/61 |
| 5,464,610 A | 11/1995 | Hayes, Jr. et al. | |
| 5,487,776 A | 1/1996 | Nimni | |
| 5,639,795 A | 6/1997 | Friedman et al. | |
| 5,661,170 A | 8/1997 | Chodosh | |
| 5,681,849 A | 10/1997 | Richter et al. | |
| 5,696,164 A | 12/1997 | Sun et al. | |
| 5,814,305 A | 9/1998 | Laugier et al. | |
| 5,856,355 A | 1/1999 | Richter et al. | |
| 5,863,527 A | 1/1999 | Hutchins et al. | |
| 5,968,986 A | 10/1999 | Dyer | |
| 6,005,001 A | 12/1999 | Richter et al. | |
| 6,007,798 A | 12/1999 | Bohn et al. | |
| 6,042,845 A | 3/2000 | Sun et al. | |
| 6,075,056 A | 6/2000 | Quigley, Jr. et al. | |
| 6,121,314 A | 9/2000 | Richter et al. | |
| 6,224,887 B1 * | 5/2001 | Samour et al. | 424/401 |
| 6,231,875 B1 | 5/2001 | Sun et al. | |
| 6,391,879 B1 | 5/2002 | Reeves | |
| 6,585,963 B1 | 7/2003 | Quan et al. | |
| 6,821,508 B2 | 11/2004 | Zatz et al. | |
| 7,074,392 B1 | 7/2006 | Friedman et al. | |
| 7,678,366 B2 * | 3/2010 | Friedman et al. | 424/61 |
| 2002/0168404 A1 | 11/2002 | Rault et al. | |
| 2005/0181999 A1 | 8/2005 | Ferrandis et al. | |

FOREIGN PATENT DOCUMENTS

| | | |
|---|---|---|
| EP | 0440298 | 8/1991 |
| EP | 0974365 | 1/2000 |
| GB | 2202743 | 10/1988 |
| WO | WO-9939680 | 8/1999 |
| WO | WO-2004/021698 A3 | 3/2004 |

OTHER PUBLICATIONS

Trepanier et al., "Current Issues iin Onychomycosis", The Annals of Pharmacotherapy, vol. 32, pp. 204-214 (1998).
International Preliminary Report on Patentability, dated Sep. 6, 2003, issued in International Application No. PCT/US2002/0011384.
Malhotra et al. "Investigation of nail permeation enhancement by chemical modification using water as a probe." J. Pharm Sci 2002; 91(2); 312-323.
Murdan, S. "Drug delivery to the nail following topical application" Int J. Pharm 2005; 236; 1-26.

* cited by examiner

*Primary Examiner* — Anand Desai
*Assistant Examiner* — Melissa Mercier
(74) *Attorney, Agent, or Firm* — Venable LLP; Keith G. Haddaway; Michael E. Nelson

(57) ABSTRACT

A topical sustained release delivery system for delivery of antifungal agents to the finger or toenails achieving high penetration through the nails by combining the antifungal agent with a keratolytic agent and a humectant. The pharmaceutical sustained release topical preparation is provided in a varnish or spray form for treating the nail and surrounding tissues, where the active ingredient is an antifungal agent, a keratolytic agent or combination thereof. The composition may further include an antibacterial, an antiviral, an antipsoriatic agents, or combinations thereof.

26 Claims, No Drawings

CONTROLLED DELIVERY SYSTEM OF ANTIFUNGAL AND KERATOLYTIC AGENTS FOR LOCAL TREATMENT OF FUNGAL INFECTIONS OF THE NAIL AND SURROUNDING TISSUES

This application is a continuation-in-part of application Ser. No. 11/313,186, filed Dec. 20, 2005, which is a continuation of application Ser. No. 09/534,960 filed on Mar. 27, 2000, now U.S. Pat. No. 7,074,392, issued Jul. 11, 2006, the contents of which are hereby incorporated by reference in their entirety.

FIELD OF THE INVENTION

The present invention relates to a sustained release composition in the form of varnish or spray comprising an antifungal agent, a keratolytic agent, or a combination of antifungal and keratolytic agents, for local treatment of fungal infections of the nails and/or surrounding tissues. The composition additionally features a humectant, water, one or more film-forming polymers, and solvents. The composition may further comprise an antibacterial agent, an antiviral agent, an antipsoriatic agent or a combination thereof.

BACKGROUND OF THE INVENTION

Fungal infections are probably the most common disorder of nails encountered in medical practice. It has been estimated that approximately 90% of elderly people have some degree of toenail involvement with fungi. Conditions of moisture and occlusion of the lower extremities favor fungal colonization. Pain may result from extreme deformity of the nail plate, but usually, the complaint is one of cosmetic appearance. The most common organisms involved in the fungal infections of the nail are *Trichophyton rubrum, Trichophyton mentagrophytes, Epidermophyton floccosum, Candida albicans, Microsporum persiccolor, Cephalosporium* species, *Aspergillus* species, and *Fusarium oxysporum*.

Fingernail infection is of far greater importance cosmetically and fortunately clears faster than toenail infection because of the more rapid growth rate of fingernails. Despite this, 4-6 months of oral griseofulvin may be required to bring about complete clearing of the fingernail. For toenail infections with extensive involvement of multiple digits, withholding treatment may be the best decision. One of the factors in the treatment decision is whether the patient is taking other medications, as griseofulvin interacts with several drugs, including anticoagulants.

Griseofulvin was the drug of choice for many years, but its low cure rate and the development of newer, more effective drugs has caused it to lose favor. Current therapeutic alternatives include itraconazole and terbinafine. These drugs are well tolerated, but attention to drug interactions is still necessary [Trepanier, E. F and Amsden, G. W. *Annals of Pharmacotherapy*, 32, 1998, 204-214].

At present, topical treatment of fungal infections directly to the nail plate is discouraging. Creams or solutions containing antifungal agents, such as imidazole derivatives, are able to deliver the active agent to the nail only for a short period of time and their permeability/penetration through the nail is very low.

U.S. Pat. No. 5,120,530 discloses an antimycotically-active nail varnish, containing an antimycotically-active substance (a morpholine derivative) and a water-insoluble film former which is a copolymerizate of acrylic acid esters and methacrylic acid esters having a low content of quaternary ammonium groups. The formulations disclosed are expected to be poorly effective because they do not contain a keratolytic agent or a humectant. As a result, the nail permeability and consequently the penetration of the antimycotic agent will be very low. In the present invention the humectant entraps the water in the film after evaporation of the organic solvents, thus enabling the solubilization of the active agents in the film. Because the water content of the nail is very low, the presence of water in the film should hydrate the nail and improve the transport of the active agents into the nail. The keratolytic agent should also help by increasing the penetration of the antifungal agent into the deeper layers of the nail.

U.S. Pat. No. 4,957,730 discloses a nail varnish comprising a water-insoluble film-forming substance and an antimycotic substance, specifically 1-hydroxy-2-pyridones. The formulations disclosed do not contain to a humectant. The nail permeability of the formulations disclosed and consequently the penetration of the active agent into the deeper layers of the nail is expected to be very low, thereby failing to achieve the desired pharmacological action and cure.

U.S. Pat. No. 5,814,305 discloses a nail preparation comprising an antifungal agent, at least one hydrophilic penetration agent, and a water-alcohol solvent medium. The formulations disclosed are disadvantageous; they are in the form of a lotion or fluid gel and do not contain a film-forming agent. As a result a sustained release action is not achieved with these formulations. The formulations disclosed are disadvantageous since such a dosage form would require multiple applications of the formulation, leading to poor patient compliance. Because of the hydrophilic character of the formulations, in the presence of water or mechanical contact, the lotion or gel will likely be washed off or removed from the nail, thereby reducing the accumulation of the active agents in the nail.

UK Patent Appl. No GB2202743 A discloses a topical antifungal composition in the form of a lotion, gel or varnish, comprising at least 1% by weight (relative to the total weight of the composition) of miconazole nitrate or econazole nitrate dissolved in a mixture of water, urea, and a water-soluble dissolving intermediary. Urea is used in the formulation as a solubility increasing agent. When the composition is in the form of a varnish it contains a resin. The lotion and gel formulations disclosed are disadvantageous since such a dosage form will not provide sustained release action and would require multiple applications of the formulation, leading to poor patient compliance. Because of the hydrophilic properties of the formulations, in the presence of water or mechanical contact, the lotion or gel will likely be washed off or removed from the nail, thereby reducing the accumulation of the active agents in the nail. The varnish formulations disclosed are disadvantageous, and do not contain a humectant. As a result, the antifungal agent will not be solubilized in the film, and the hydration of the nail and transport of the antifungal agent through the nail will be very low, preventing achievement of the desired pharmacological action. In addition, UK Patent Appl. No GB2202743 A describes a delivery system specific for miconazole nitrate or econazole nitrate, which is not therefore a general delivery system for other antifungal agents.

None of these prior art references suggest or disclose the use of a combination of antifungal agent, keratolytic agent, and a humectant (glycerol at high concentrations). This combination is particularly advantageous because it increases the penetration of the active antifungal agent through the nail and 10 thus provides better pharmacological action.

U.S. Pat. No. 5,346,692 discloses a nail lacquer for treating onychomycosis, which comprises (a) a film former agent, (b)

at least one antimycotically active substance, (c) urea; and (d) a solvent which comprises (i) 50-70 wt. % of acetone; and (ii) 30-50 wt. % of 90 volume % aqueous ethanol. The formulations disclosed are disadvantageous since they use high concentrations of the antimycotically active substance and urea, thereby causing unwanted adverse effects (for example irritation and burning) which leads to poor compliance.

The formulations disclosed do not contain glycerol which would entrap the water in the film after evaporation of the organic solvents. The presence of water in the film enables the active agents to be maintained in a soluble form that is readily available for pharmacological action. Since the water content in the nail is very low, the presence of water in the film hydrates the nail so that the active agents can be delivered into deeper layers of the nail.

There is thus a need for, and it would be useful to have, a better formulation, containing low concentrations of the antifungal and keratolytic agents, to deliver pharmacologically active agents to the nail for the treatment of fungal infection thereof. This formulation would feature a film-forming agent and a humectant, for example, glycerol, for trapping water in the film formed on the nail, and the water so trapped would hydrate the nail for delivery of the agent thereto.

This formulation would be lower in cost because of the lower concentrations of the antifungal and keratolytic agents. Additionally, such formulation would reduce the unwanted side effects caused by high concentrations of the antifungal and keratolytic agents and yet be suitable for treatment of fungal infections of the nail and surrounding tissues.

SUMMARY OF THE INVENTION

The present invention provides a pharmaceutical sustained release preparation in a varnish or spray form for local treatment of the nail and surrounding tissues, where the active ingredient is an antifungal agent, a keratolytic agent, or a combination of an antifungal and a keratolytic agent. The composition may further comprise an antibacterial, an antiviral, an antipsoriatic agent or combinations thereof.

In a first embodiment the present invention provides a sustained release nail varnish composition comprising:
  (a) a pharmaceutically effective agent;
  (b) a humectant;
  (c) water;
  (d) less than about 7.5% (w/w) based on the total weight of the composition, of a polymeric film-forming agent;
  (e) at least one additional excipient; and
  (f) a solvent system including at least one volatile solvent.

In a second embodiment the present invention provides a sustained release nail varnish composition comprising:
  (a) an antifungal agent;
  (b) a keratolytic agent;
  (c) a humectant;
  (d) water;
  (e) a polymeric film-forming agent;
  (f) at least one additional excipient; and
  (g) a solvent system including at least one volatile solvent.

Embodiments of the invention include a sustained release therapeutic nail varnish for treating a human for a fungal infection, onychomycoses, psoriasis and/or chronic paronycia of the nail and/or surrounding tissue, having:
  a. a pharmaceutically effective amount of a pharmaceutical ingredient;
  b. about 0.3% to about 2% of a keratolytic agent;
  c. about 1% to about 15% of a humectant wherein the humectant is sorbitol, glycerol or a mixture thereof;
  d. water in an amount of about 0.1% to about 5% of the varnish solution;
  e. about 2% to about 15% of a hydrophobic methacrylic polymer; and
  f. a volatile solvent in an amount of about 60% to about 90%, relative to the total weight of the composition.

Other embodiments of the invention include a sustained release therapeutic nail varnish for treating a human for a fungal infection, onychomycoses, psoriasis and/or chronic paronycia of the nail and/or surrounding tissue, having:
  a. a pharmaceutically effective amount of a pharmaceutical ingredient;
  b. a keratolytic agent in an amount of 0.3% to less than about 1% of the varnish solution;
  c. a humectant wherein the humectant is sorbitol, glycerol or a mixture thereof, and the humectant is present in a concentration of about 5% to about 35% (w/w), based on the weight of the non-volatile components;
  d. water in an amount of 0.5 to less than about 5% of the varnish solution;
  e. a hydrophobic methacrylic polymer in an amount of about 8% to about 35% based on the total weight of the non-volatile components; and
  f. a volatile solvent in an amount of about 60% to about 90%, relative to the total weight of the composition; where the weight ratio of polymer to the keratolytic agent is in the range from about 1:0.01 to about 1:1.

Embodiments of the invention include methods of treating a human for a fungal infection, onychomycoses, psoriasis and/or chronic paronycia of the nail and/or surrounding tissue, comprising topically applying to the surface of a nail, a nail varnish comprising:
  a. a pharmaceutically effective amount of a pharmaceutical ingredient;
  b. about 0.3% to about 2% of a keratolytic agent;
  c. about 1% to about 15% of a humectant wherein the humectant is sorbitol, glycerol or a mixture thereof;
  d. water in an amount of about 0.1% to about 5% of the varnish solution;
  e. about 2% to about 10% of a hydrophobic methacrylic polymer; and
  f. a volatile solvent in an amount of about 60% to about 90%, relative to the total weight of the composition.

In some embodiments the pharmaceutically effective agent is selected from the group consisting of an antifungal agent, a keratolytic agent, and mixtures thereof.

In some embodiments the antifungal agent is selected from the group consisting of amphothericin B, butefanine, butoconazole, carbol-fuchsin, ciclopirox, clioquinol, clotrimazole, econazole, gentian violet, ketoconazole, miconazole, naftifine, nystatin, oxiconazole, sodium thiosulfate, terbinafine, terconazole, tolnaftate, undecylenic acid, therapeutically acceptable salts thereof, derivatives thereof, and mixtures thereof.

In some embodiments, the concentration of the antifungal agent in the varnish is between about 0.3% (w/w) and about 5% (w/w). In other embodiments, the concentration of the antifungal agent in the varnish solution is between about 1% (w/w) and about 5% (w/w). In some embodiments the concentration of the antifungal agent in the varnish solution is less than about 1% (w/w).

In some embodiments, the antifungal agent is present in a concentration of about 0.3% (w/w) to about 25% (w/w) based on the weight of the non-volatile components. In some embodiments, the antifungal agent is present in a concentration of about 1% (w/w) to about 20% (w/w) based on the weight of the non-volatile components. In some embodiments the antifungal agent is present in concentration of less than about 5% (w/w) based on the weight of the non-volatile components.

In some embodiments the keratolytic agent is selected from the group consisting of urea, sulfur, salicylic acid, podophyllum resin, and mixtures thereof.

In some embodiments, the concentration of the keratolytic agent in the varnish solution is between about 0.3% (w/w) and about 5% (w/w). In some embodiments, the concentration of the keratolytic agent in the varnish solution is between about 0.3% (w/w) and about 2% (w/w). In some embodiments the concentration of the keratolytic agent in the varnish solution is less than about 1% (w/w).

In some embodiments, the keratolytic agent is present in concentration of from about 0.05% to about 10% (w/w), based on the weight of the non-volatile components. In some embodiments, the keratolytic agent is present in concentration of from about 0.05% to about 8% (w/w), based on the weight of the non-volatile components. In some embodiments the keratolytic agent is present in concentration of from about 0.05% to about 5% (w/w), based on the weight of the non-volatile components.

In some embodiments the pharmaceutically effective agent further comprises an antibacterial, an antiviral, an antipsoriatic agent, or mixtures thereof.

In some embodiments the antibacterial agent is selected from the group consisting of bacitracin, clindamycin, erythromycin, gentamicin, mupirocin, neomycin, tetracyclines, polymyxin B, benzalkonium chloride, boric acid, hexachlorophene, iodine, iodoquinol, mafenide, mercury ammoniated, metronidazole, nitrofurazone, selenium sulfide, silver sulfadiazine, salts thereof, derivatives thereof, and mixtures thereof.

In some embodiments the concentration of the antibacterial agent in the varnish solution is from about 0.01% to about 1% (w/w).

In some embodiments the antibacterial agent is present in concentration of from about 0.05% to about 5% (w/w), based on the weight of the non-volatile components.

In some embodiments the antiviral agent is selected from the group consisting of acyclovir, amantadine, cidofovir, famciclovir, foscarnet, ganciclovir, palivizumab, penciclovir, ribavirin, rimantadine, valcyclovir, salts thereof, derivatives thereof, and mixtures thereof.

In some embodiments the concentration of the antiviral agent in the varnish solution is from about 0.08% to about 0.8% (w/w).

In some embodiments the antiviral agent is present in concentration of from about 0.8% to about 8% (w/w), based on the weight of the non-volatile components.

In some embodiments the antipsoriatic agent is selected from the group consisting of alclometasone, amcinonide, betamethasone, clobetasol, clocortolone, desonide, desoximetasone, diflorasone, fluocinolone, fluocinonide, flurandrenolide, halcinonide, hydrocortisone, mometasone, prednicarbate and triamcinolone, salts thereof, derivatives thereof, and mixtures thereof.

In some embodiments the concentration of the antipsoriatic agent in the varnish solution is from about 0.02% to about 2% (w/w).

In some embodiments the antipsoriatic agent is present in concentration of from about 0.1% to about 10% (w/w), based on the weight of the non-volatile components.

In some embodiments the humectant is selected from the group consisting of glycerol, sorbitol, and mixtures thereof.

In some embodiments, the concentration of the humectant in the varnish solution is from about 1% to about 15% (w/w).

In some embodiments the concentration of the humectant in the varnish solution is from about 3% to about 15% (w/w).

In some embodiments the humectant is present in concentration of from about 5% to about 35% (w/w), based on the weight of the non-volatile components.

In some embodiments, the water concentration in the varnish solution is between about 0.1% (w/w) and about 5% (w/w). In some embodiments the water concentration in the varnish solution is less than about 5% (w/w).

In some embodiments the concentration of the water in the film is from about 0.4% to about 25% (w/w).

In some embodiment the polymeric film-forming agent is selected from the group consisting of hydrophobic (water insoluble) polymers.

In some embodiments the hydrophobic (water insoluble) polymer is selected from the group consisting of hydrophobic cellulose derivatives, hydrophobic methacrylic polymers, cellulose acetate phthalate, shellac, derivatives thereof, and mixtures thereof.

In some embodiments the hydrophobic cellulose derivative is selected from the group consisting of ethyl cellulose of any acceptable molecular weight.

In some embodiments the hydrophobic methacrylic polymer is selected from the group consisting of methacrylic acid copolymer type B to (USP/NF), methacrylic acid copolymer type C (USP/NF), ammonio methacrylate copolymer type B (USP/NF) and ammonio methacrylate copolymer type A (USP/NF), derivatives thereof, and mixtures thereof.

In some embodiments the hydrophobic methacrylic polymer is selected from the group consisting of Eudragit S, Eudragit L, Eudragit RS, and Eudragit RL manufactured by Rohm Pharma, but hydrophobic methacrylic polymers from other sources can also be used.

In some embodiments, the concentration of the polymer film forming agent in the varnish solution is from about 2% (w/w) to about 15% (w/w). In some embodiments, the concentration of the polymer film forming agent in the varnish solution is from about 3% (w/w) to about 10% (w/w). In some embodiment the concentration of the polymeric film-forming agent in the varnish solution is less than about 7.5% (w/w).

In some embodiments, the polymeric film-forming agent is present in concentration of from about 5% to about 50% (w/w), based on the weight of the non-volatile components. In some embodiments, the polymeric film-forming agent is present in concentration of from about 10% to about 50% (w/w), based on the weight of the non-volatile components. In some embodiments, the polymeric film-forming agent is present in concentration of from about 20% to about 50% (w/w), based on the weight of the non-volatile components. In some embodiments the polymeric film-forming agent is present in concentration of from about 8% to about 35% (w/w), based on the weight of the non-volatile components.

In some embodiments, the weight ratio of polymer to the antifungal agent is in the range from about 1:0.01 to about 1:1. In some embodiments, the weight ratio of polymer to the antifungal agent is in the range from about 1:0.05 to about 1:0.8. In some embodiments the weight ratio of polymer to the antifungal agent is in the range from about 1:0.01 to about 1:0.3.

In some embodiments the weight ratio of polymer to the keratolytic agent is in the range from about 1:0.01 to about 1:1.

In some embodiments the weight ratio of polymer to antibacterial agent is in the range from about 1:0.01 to about 1:0.3.

In some embodiments the weight ratio of polymer to antiviral agent is in the range from about 1:0.02 to about 1:0.2.

In some embodiments, the weight ratio of polymer to antipsoriatic agent is in the range from about 1:0.006 to about 1:0.3. In some embodiments the weight ratio of polymer to antipsoriatic agent is in the range from about 1:0.006 to about 1:0.15.

In some embodiments the at least one additional excipient is selected from a group consisting of plasticizers.

In some embodiments the plasticizer is selected from the group consisting of dibutyl sebacate, diethyl phthalate, lanolin alcohols, mineral oil, petrolatum, polyethylene glycol, propylene glycol, triacetin, triethyl citrate, and mixtures thereof.

In some embodiments the concentration of the plasticizer in the varnish solution is from about 0.1% to about 2% (w/w).

In some embodiments the plasticizer is present in concentration of from about 0.5% to about 10% (w/w), based on the weight of the non-volatile components.

In some embodiments the weight ratio of the plasticizer to the polymer is in the range from about 0.04:1 to about 0.3:1.

In some embodiments the volatile solvent is selected from the group consisting of an alcohol, a ketone, an ester, and mixtures thereof.

In some embodiment the alcohol is selected from the group consisting of ethanol, isopropyl alcohol, methanol and mixtures thereof.

In some embodiments the ketone is acetone.

In some embodiments, the ester is ethyl acetate.

In some embodiments, the volatile solvent is a mixture of isopropyl alcohol and ethyl acetate. In some embodiments, the volative solvent is a mixture of ethyl acetate and acetone. In some embodiments the volatile solvent is a mixture of acetone and isopropyl alcohol.

In some embodiments the volatile solvent is present in an amount of from about 60% to about 90% (w/w), relative to the total weight of the composition.

In some embodiments the volumetric ratio of acetone to isopropyl alcohol is in the range from about 1:4 to about 4:1.

In some embodiments the solvent system further includes at least one non-volatile solvent selected from the group consisting of benzyl alcohol, benzyl benzoate, corn oil, cottonseed oil, ethyl oleate, glycerin, glycofural, isopropyl myristate, isopropyl palmitate, mineral oil, peanut oil, polyethylene glycol, propylene glycol, propylene carbonate, sesame oil, soybean oil, water, and mixtures thereof.

In some embodiments the composition may further comprise preservatives, antioxidants, surfactants and coloring agents.

A further embodiment of the present invention provides a method of preparing a sustained release varnish or spray formulation for treating the nail and surrounding tissues, comprising the steps of (a) preparing a solution including at least one volatile solvent; (b) adding water to the solution prepared in (a); (c) dissolving the pharmaceutically effective agents, and excipients in the solution prepared in (b); (d) adding the humectant to the solution prepared in (c) when the formulation ingredients are completely dissolved; and (e) dissolving the polymeric film-forming agents in the solution prepared in (d).

DETAILED DESCRIPTION

The present invention is a sustained release delivery system for antifungal agents achieving high penetration through the nail by combining the antifungal agent with a keratolytic agent and a humectant.

DEFINITIONS

By "varnish solution" is meant the total composition before evaporation of the volatile components.

By "film" is meant the non-volatile components, which are remained after evaporation of the volatile components of the varnish solution.

By "concentration or amount relative to the total weight of the composition" is meant concentration in the varnish solution, before application to the nail or before evaporation of the volatile components.

By "concentration or amount based on the weight of the non-volatile components" is meant concentration based on the weight of the components remaining after evaporation of the volatile components (i.e. concentration in the film).

The present invention provides a topical, sustained release pharmaceutical preparation in a varnish or spray form for treating the nail and surrounding tissues, where, for example, the active ingredient is an anti-fungal agent, a keratolytic agent, or a combination of an antifungal and a keratolytic agent. The composition may further comprise an antibacterial, an antiviral, an antipsoriatic agent or combinations thereof.

The composition features an effective quantity of at least one antifungal agent, an effective quantity of at least one keratolytic agent, a humectant, water, polymers, optionally at least one additional pharmaceutical excipient and finally a solvent medium. The additional excipients include plasticizers. The composition may further comprise an effective quantity of at least one antibacterial, antiviral, antipsoriatic agent or combinations thereof.

The delivery system is in the form of a solution or spray for self-application by the patient. After application of the solution to the nail surface, the solvent evaporates and a film/coating is formed on the surface. The film/coating has the capacity to release the antifungal and keratolytic agents in therapeutic levels over a prolonged period of time.

The combination of an antifungal and keratolytic agent is advantageous because it increases the penetration of the antifungal agent through the nail. Because the amount of water in the nail is very low, it is essential to achieve relatively high concentrations of water in the film. The humectant is added to the present invention in order to retain water in the film after the evaporation of the organic solvents. The film formed after evaporation of the volatile solvents contains the pharmaceutically effective agents, polymers, humectant, the water entrapped by the humectant, and additional non-volatile excipients. The presence of water in the film is maintains the active agents in a saturated-reservoir solution, thus enabling the solubilized agents to be released in a controlled manner into the nail, which can be of significant importance.

The combination of glycerol (humectant), water and low concentrations of keratolytic and antifungal agents, used in the present invention, are particularly advantageous. The water entrapped in the film by the glycerol hydrates the nail and enables low concentrations of the keratolytic agent to be used in order to increase the permeability of the nail. Consequently lower concentrations of the antifungal agent can be adequate in order to diffuse through the nail and provide the desired pharmacological action. Such a combination would reduce the unwanted side effects caused by high keratolytic agent and antifungal agent concentrations. An additional advantage of the use of low keratolytic agent and antifungal agent concentrations is the reduction of the product price.

The antifungal agents are, for example, amphothericin B, butefanine, butoconazole, carbol-fuchsin, ciclopirox, clioquinol, clotrimazole, econazole, gentian violet, ketoconazole, miconazole, naftifine, nystatin, oxiconazole, sodium thiosulfate, terbinafine, terconazole, tolnaftate, undecylenic acid, therapeutically acceptable salts thereof, derivatives thereof, and mixtures thereof. In some embodiments, the antifungal agents may be clotrimazole, miconazole nitrate or terbinafine. In some specific embodiments, the antifungal agent is miconazole nitrate. In some specific embodiments, the antifungal agent is tebinafine or therapeutically acceptable salts thereof. In some embodiments, the concentration of the antifungal agent in the varnish is between about 0.3% (w/w) and about 5% (w/w). In other embodiments, the concentration of the antifungal agent in the varnish solution is between about 1% (w/w) and about 5% (w/w). In some embodiments the concentration of the antifungal agent in the varnish solution is less than about 1% (w/w). In some embodiments the concentration of the antifungal agents in the varnish solution is less than about 1% (w/w) or about 0.3-0.9% (w/w).

In some embodiments, the antifungal agent is present in a concentration of about 0.3% (w/w) to about 25% (w/w) based on the weight of the non-volatile components. In some embodiments, the antifungal agent is present in a concentration of about 1% (w/w) to about 20% (w/w) based on the weight of the non-volatile components. In some embodiments the antifungal agent is present in concentration of less than about 5% (w/w) based on the weight of the non-volatile components. In some embodiments, the concentration of the antifungal agents based on the weight of the non-volatile components is less than about 5% (w/w) or about 0.3-4.7% (w/w).

The keratolytic agents are added to the present invention in order to increase the permeability of and penetration into the nail.

The keratolytic agents are, for example, urea, sulfur, salicylic acid, podophyllum resin, and mixtures thereof. In some embodiments, the keratolytic agent is urea. In some embodiments, the concentration of the keratolytic agent in the varnish solution is between about 0.3% (w/w) and about 5% (w/w). In some embodiments, the concentration of the keratolytic agent in the varnish solution is between about 0.3% (w/w) and about 2% (w/w). In some embodiments the concentration of the keratolytic agents in the varnish solution is less than about 1% (w/w) or about 0.3-0.9% (w/w).

In some embodiments, the keratolytic agent is present in concentration of from about 0.05% to about 10% (w/w), based on the weight of the non-volatile components. In some embodiments, the keratolytic agent is present in concentration of from about 0.05% to about 8% (w/w), based on the weight of the non-volatile components. In some embodiments, the concentration of the keratolytic agent based on the weight of the non-volatile components is in the range from about 0.05% to about 5% (w/w).

The antibacterial agents are, for example, bacitracin, clindamycin, erythromycin, gentamicin, mupirocin, neomycin, tetracyclines, polymyxin B, benzalkonium chloride, boric acid, hexachlorophene, iodine, iodoquinol, mafenide, mercury ammoniated, metronidazole, nitrofurazone, selenium sulfide, silver sulfadiazine, salts thereof, derivatives thereof, and mixtures thereof. In some embodiments, the concentration of the antibacterial agents in the varnish solution is in the range from about 0.01% to about 1% (w/w), or about 0.2-0.8% (w/w). In some embodiments the concentration of the antibacterial agents based on the weight of the non-volatile components is in the range from about 0.05% to about 5% (w/w) or about 1.5-4.5% (w/w).

The antiviral agents are, for example, acyclovir, amantadine, cidofovir, famciclovir, foscarnet, ganciclovir, palivizumab, penciclovir, ribavirin, rimantadine, valcyclovir, salts thereof, derivatives thereof, and mixtures thereof. In some embodiments the concentration of the antiviral agents in the varnish solution is in the range from about 0.08% to about 0.8% (w/w) orb about 0.2-0.6% (w/w). In some embodiments the concentration of the antiviral agents based on the weight of the non-volatile components is in the range from about 0.8% to about 8% (w/w) or about 2-6% (w/w).

The antipsoriatic agents are, for example, alclometasone, amcinonide, betamethasone, clobetasol, clocortolone, desonide, desoximetasone, diflorasone, fluocinolone, fluocinonide, flurandrenolide, halcinonide, hydrocortisone, mometasone, prednicarbate, triamcinolone, salts thereof, derivatives thereof, and mixtures thereof. In some embodiments, the antipsoriatic agent is clobetasol. In some embodiments the concentration of the antipsoriatic agents in the varnish solution is in the range from about 0.02% to about 2% (w/w) or about 0.2-1.5% (w/w). In some embodiments the concentration of the antipsoriatic agents based on the weight of the non-volatile components is in the range from about 0.1% to about 10% (w/w) or about 1-7.5% (w/w).

Since the water content of the nail is very low it is important to achieve relatively high concentrations of water in the delivery system. The humectant is added to the varnish solution in order to hold the water in the film after evaporation of the organic solvents. The presence of water in the film hydrates the nail so that the active agents can be delivered into the deeper layers of the nail. The humectant is, in some embodiments, glycerol, sorbitol, and mixtures thereof. In some embodiments, the humectant is glycerol. In some embodiments, the concentration of the humectant in the varnish solution is from about 1% to about 15% (w/w). In some embodiments, the concentration of the humectant in the varnish solution is greater than about 1%, greater than about 2% or greater than about 3%. In some embodiments, the concentration of the humectant in the varnish solution is in the range from about 3% to about 15% (w/w), or about 4-10% (w/w).

In some embodiments, the concentration of the humectant based on the weight of the non-volatile components is in the range from about 5% to about 35% (w/w), or about 10-30% (w/w).

Although glycerol can serve at lower concentrations (less than 2% w/w based on the total weight of the composition) as a plasticizer, at this lower concentration range glycerol is not efficient as a humectant and therefore higher concentrations (above about 2% or above about 3% (w/w)) of glycerol are required in order to be effective as a humectant.

In some embodiments, the water concentration in the varnish solution is between about 0.1% (w/w) and about 5% (w/w). In some embodiments the water concentration in the varnish solution is less than about 5% (w/w), about 0.5-4.5% (w/w) or about 1-4.5% (w/w). In some embodiments, the concentration of the water in the film is in the range from about 0.4% to about 25% (w/w), about 0.8-20% (w/w), or about 2-18% (w/w).

The delayed release polymeric film-forming agents are, for example, hydrophobic (water insoluble) polymers. The hydrophobic (water insoluble) polymers include hydrophobic cellulose derivatives, hydrophobic methacrylic polymers, cellulose acetate phthalate, shellac, derivatives thereof and mixtures thereof. The hydrophobic cellulose derivatives can be, for example, ethyl cellulose of any acceptable molecular weight.

The hydrophobic methacrylic polymers are, for example, methacrylic acid copolymer type B (USP/NF), methacrylic acid copolymer type C (USP/NF), ammonio methacrylate copolymer type B (USP/NF) and ammonio methacrylate copolymer type A (USP/14F), derivatives thereof, and mixtures thereof. The hydrophobic methacrylic polymers are, for example, Eudragit S, Eudragit L, Eudragit RS, and Eudragit RL manufactured by Rohm Pharma, but hydrophobic methacrylic polymers from other sources can also be used. The polymers provide a uniform film, retard the release rate of the drugs (agents), and can be mixed in regulated amounts to attain the desired drug release characteristics.

In some embodiments, the concentration of the polymer film forming agent in the varnish solution is from about 2% (w/w) to about 15% (w/w). In some embodiments, the concentration of the polymer film forming agent in the varnish solution is from about 3% (w/w) to about 10% (w/w). In some embodiment, the concentration of the polymeric film-forming agent in the varnish solution is less than about 7.5% (w/w). In some embodiments, the polymeric film-forming agent is present in concentration of from about 5% to about 50% (w/w), based on the weight of the non-volatile components. In some embodiments, the polymeric film-forming agent is present in concentration of from about 10% to about 50% (w/w), based on the weight of the non-volatile components. In some embodiments, the polymeric film-forming agent is present in concentration of from about 20% to about 50% (w/w), based on the weight of the non-volatile components. In some embodiments the concentration of the polymeric film-forming agent based on the total weight of the non-volatile components is in the range from about 8% to about 35% (w/w), about 18-30% (w/w), or about 23-27% (w/w).

In some embodiments, the weight ratio of polymer to the antifungal agent is in the range from about 1:0.01 to about 1:1. In some embodiments, the weight ratio of polymer to the antifungal agent is in the range from about 1:0.05 to about 1:0.8. In some embodiments, the weight ratio of polymer to the antifungal agent is in the range from about 1:0.01 to about 1:0.3, or in the range from about 1:0.06 to about 1:0.25.

In some embodiments, the weight ratio of polymer to the keratolytic agent is in the range from about 1:0.01 to about 1:1, or in the range from about 1:0.05 to about 1:1

In some embodiments, the weight ratio of polymer to antibacterial agent is in the range from about 1:0.01 to about 1:0.3, or in the range from about 1:0.05 to about 1:0.25.

In some embodiments, the weight ratio of polymer to antiviral agent is in the range from about 1:0.02 to about 1:0.2, or in the range from about 1:0.05 to about 1:0.2.

In some embodiments, the weight ratio of polymer to antipsoriatic agent is in the range from about 1:0.006 to about 1:0.3. In some embodiments, the weight ratio of polymer to antipsoriatic agent is in the range from about 1:0.006 to about 1:0.15, or in the range from about 1:0.01 to about 1:0.15.

Plasticizers are added to the varnish solution in order to enhance the plasticity of the film formed and to modify the sustained release characteristics of the polymer. The plasticizer is, for example, dibutyl sebacate, diethyl phthalate, lanolin alcohols, mineral oil, petrolatum, polyethylene glycol, propylene glycol, triacetin, triethyl citrate, or mixtures thereof. In some embodiments, the plasticizer is polyethylene glycol with molecular weight of 300-6000.

In some embodiments, the concentration of the plasticizer in the varnish solution is in the range from about 0.1% to about 2% (w/w), or about 0.2-1% (w/w), or about 0.4-0.8% (w/w). In some embodiments, the concentration of the plasticizer based on the total weight of the non-volatile components is in the range from about 0.5% to about 10% (w/w), about 1-5% (w/w), or about 2-3% (w/w).

In some embodiments, the weight ratio of the plasticizer to the polymer is in the range from about 0.04:1 to about 0.3:1. In other embodiments, the weight ratio of the plasticizer to polymer is in the range from about 0.05:1 to about 0.2:1.

In some embodiments, the volatile solvent is selected from the group consisting of an alcohol, a ketone, an ester and mixtures thereof. In some embodiments, the ester is, for example, ethyl acetate, methyl propionate, or butyl acetate. In some embodiments, the alcohol is, for example, ethanol, isopropyl alcohol, methanol and mixtures thereof. The ketone is, for example, acetone or methyl ethyl ketone.

In some embodiments, the volatile solvent is a mixture of isopropyl alcohol and ethyl acetate. In some embodiments, the volative solvent is a mixture of ethyl acetate and acetone. In some embodiments the volatile solvent is a mixture of acetone and isopropyl alcohol.

In some embodiments, the volatile solvent is present in an amount of from about 60% to about 90% (w/w), or from about 70% to about 85% (w/w) relative to the total weight of the composition.

In some embodiments, the volumetric ratio of acetone to isopropyl alcohol is in the range from about 1:4 to about 4:1 or from about 1:3 to about 3:1. In some embodiments, the volumetric ratio of acetone to ethyl acetate is in the range from about 1:4 to about 4:1 or from about 1:3 to about 3:1. In some embodiments, the volumetric ratio of isopropyl alcohol to ethyl acetate is in the range from about 1:4 to about 4:1 or from about 1:3 to about 3:1.

In some embodiments, the solvent system further includes at least one non-volatile solvent.

The at least one non-volatile solvent is, for example, benzyl alcohol, benzyl benzoate, corn oil, cottonseed oil, ethyl oleate, glycerin, glycofural, isopropyl myristate, isopropyl palmitate, mineral oil, peanut oil, polyethylene glycol, propylene glycol, propylene carbonate, sesame oil, soybean oil, water, and mixtures thereof.

Optional ingredients include at least one additive chosen from among the group consisting of preservatives, antioxidants, surfactants and coloring agents which are well known in the art.

The preservative is, for example, benzoic acid, benzyl alcohol, bronopol, butyl paraben, chlorbutanol, chlorocresol, cresol, ethyl paraben, methyl paraben, phenol, propyl paraben, sodium benzoate, sodium propionate, sorbic acid, or mixtures thereof.

The antioxidant is, for example, alpha tocopherol, ascorbic acid, ascorbyl palmitate, butylated hydroxyanisole, butylated hydroxytoluene, fumaric acid, malic acid, propyl gallate, sodium ascorbate, sodium metabisulfite, or mixtures thereof.

The surfactant is, for example, cetrimide, sodium lauryl sulfate, docusate sodium, glyceryl monooleate, polysorbates, sorbitan esters, or mixtures thereof.

The coloring agent is, for example, amaranth, brilliant blue, caratenoids, carmoisine, curcumin, eosine, erythrosine, fluorescein, rhodoxantin, tetrazine, or mixtures thereof.

The composition prepared according to the present invention may advantageously be presented in the form of varnish or spray.

For a better understanding of the object of the invention, several examples of this composition are described; these are intended as purely illustrative examples without any intention of being limiting. It is to be understood that the invention is not limited in its application to the details of construction and the arrangement of the components set forth in the following description. The invention includes other embodiments and can be practiced or implemented in various ways. It is also to be understood that the phraseology and terminology employed herein is for the purpose of description only and should not be regarded as limiting.

EXAMPLES OF THE FORMULATIONS OF THE PRESENT INVENTION

Example 1

The formulations of the present invention were all prepared according to the general procedure which is described below (Preparation of Varnish).

Antifungal Nail Varnish Sustained Release Formulations (Quantities are in % (w/w))

|  | Formulation No | | | | | | | | | | | | | | |
|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 |
| Urea | 0.7 | 0.7 | 0.7 | 0.7 | 0.8 | 0.8 | 0.8 | 0.7 | 0.7 | 0.7 | 0.7 | 0.7 | 0.9 | 0.9 | 0.8 |
| Clotrimazole |  |  |  |  |  |  |  |  |  |  | 0.9 | 0.8 | 0.4 | 0.9 | 0.8 |
| Miconazole nitrate | 0.8 | 0.8 | 0.8 | 0.8 | 0.8 | 0.8 | 0.9 | 0.8 | 0.98 | 0.4 |  |  |  |  |  |
| Ethyl Cellulose |  |  | 0.8 | 0.8 | 3.4 | 4.2 | 4.3 |  |  |  |  |  |  | — |  |
| Eudragit S | 7.3 | 6.5 | 6.2 | 5.0 |  |  |  |  | 7.3 | 7.4 | 7.3 | 7.3 | 7.4 | 7.3 | 7.3 |
| Eudragit RS |  |  |  |  |  |  | 0.9 | 7.3 |  |  |  |  |  |  |  |
| Water | 4.0 | 4.1 | 4.1 | 4.1 | 4.3 | 4.2 | 4.4 | 4.1 | 4.1 | 4.1 | 4.0 | 4.0 | 4.0 | 4.1 | 4.1 |
| Acetone | 61.3 | 61.8 | 61.5 | 62.3 | 63.9 | 63.3 | 65.6 | 61.3 | 61.2 | 61.5 | 61.2 | 61.2 | 61.5 | 61.0 | 61.1 |
| Isopropyl alcohol | 20.4 | 20.6 | 20.5 | 20.8 | 213 | 21.1 | 21.8 | 20.4 | 20.4 | 20.5 | 20.4 | 20.4 | 20.5 | 20.3 | 20.4 |
| PEG 400 | 0.4 | 0.4 | 0.4 | 0.4 | 0.4 | 0.4 | 0.4 | 0.4 | 0.4 | 0.4 | 0.4 | 0.4 | 0.4 | 0.4 | 0.4 |
| Glycerol | 4.9 | 5.0 | 4.9 | 5.0 | 5.1 | 5.1 | 5.2 | 4.9 | 4.9 | 4.9 | 4.9 | 4.9 | 4.9 | 4.9 | 4.9 |

General Procedure for the Varnish Preparation

A mixture of acetone and isopropyl alcohol was prepared. Water was added to the organic mixture and then urea was dissolved in the solution. PEG and the antifungal agent (miconazole nitrate) were added and dissolved in the solution. When the antifungal agent was completely dissolved, the humectant was added to the solution. Thereafter the polymer was added to the solution. The solution was brought to the final weight using the organic mixture prepared in the first step. All the steps of the varnish preparation were performed while continuously stirring the solution.

Film Preparation

The films were cast from the varnish solutions onto glass surfaces (petri dishes). The solvent was allowed to evaporate for 24 h and the film was removed from the surface. Films of $100 \times 10^{-4}$ cm thickness were prepared and used for testing of (1) water residue in the film (2) dissolution rate of the active agents from the film and (3) sustained antifungal activity in vitro.

Example 2

Determination of the Water Residue in the Films

All the films were tested using the Karl Fisher method to determine the water content.

| Formulation No.* | Water in dry film, % (w/w) |
|---|---|
| 1 | 12 |
| 1** | 5 |
| 6 | 13 |
| 6** | 4 |
| 7 | 13 |
| 7** | 3 |

*The formulation No. is related to the table in Example 1
**without glycerol

These results show that the humectant is able to hold the water in the dry film.

Example 3

Dissolution Rates of the Active Agents (Miconazole Nitrate and Urea)

Films were cut to a circular form, 2.54 cm² in area, and were weighed accurately. Film thickness was measured with a micrometer. The membranes were attached to a specially designed dissolution basket in which only one surface of the membrane was exposed to the dissolution medium. 150 ml of 1% sodium lauryl sulfate solution served as the dissolution medium. The dissolution rates were measured in a Van-Kel (VK 7000) dissolution test apparatus at 32° C. and 100 rpm rotating speed.

Aliquots were withdrawn at various times and replaced by fresh solvent, with corrections being applied in the calculations. The amount of drug released was determined spectrophotometrically at 230 nm for miconazole and 564 nm (color reaction) for urea.

The dissolution rates of miconazole nitrate and urea are presented in the following tables:

Dissolution Rates of Miconazole Nitrate from the Formulations Described in Example 1

|  | Amount drug released (%) | | | | |
|---|---|---|---|---|---|
| Formulation | 60 min | 120 min | 240 min | 480 min | 1440 min |
| 1 | 7.5 | 21.2 | 37.8 | 50.2 | 96.1 |
| 6 | 6.5 | 11.8 | 20.8 | 30.5 | 61.2 |
| 7 | 5.1 | 8.4 | 14.2 | 20.6 | 52.4 |
| 14 | 7.0 | 16.0 | 21.8 | 28.9 | 70.1 |

Dissolution Rates of Urea from the Formulations Described in Example 1

|  | Amount drug released (%) | | | | |
|---|---|---|---|---|---|
| Formulation | 60 min | 120 min | 240 min | 480 min | 1440 min |
| 1 | 15.8 | 33.4 | 59.7 | 96.2 |  |
| 6 | 10.2 | 26.1 | 42.5 | 65.0 | 99.8 |
| 7 | 8.6 | 19.1 | 38.9 | 49.2 | 95.1 |
| 14 | 11.2 | 24.0 | 46.2 | 61.0 | 98.6 |

The results show that both miconazole nitrate and urea are released from the films in a controlled manner. The release of urea is higher than miconazole nitrate, this can be explained by the higher solubility and lower molecular weight of urea, compared to miconazole nitrate. The faster release of urea compared to miconazole nitrate is advantageous since higher concentrations of urea increases the permeability of the nail thereby enabling better penetration of the antifungal agent (miconazole) into deeper layers of the nail.

Example 4

Sustained Release Activity of Clotrimazole and Miconazole Nitrate In Vitro

A strain of *Saccharomyces cerevisiea* was used in this study. A 1:10 dilution of a stock suspension of the above organism was mixed with mycological culture medium and poured into petri dishes. 5 mm diameter discs of the film (Formulation No 1, 6, 7, 14) containing clotrimazole or miconazole nitrate were placed on the hardened medium and incubated for 24 h at 37° C. Thereafter the films were transferred to another set of petri dishes containing the same medium plus *Saccharomyces cerevisiea*.

Inhibition zones were recorded after incubation period of 24 hours. All samples were tested in triplicate. The mean inhibition zone sizes are summarized in the following table.

Inhibition zones of *S. cerevisiea* growth by sustained release films containing miconazole nitrate (formulation No 1, 6, 7) and clotrimazole (formulation No 14).

| | Inhibition Zone (mm) Formulation No | | | |
|---|---|---|---|---|
| Time | 1 | 6 | 7 | 14 |
| 24 hrs | 30.67 | 28.77 | 28.37 | 28.64 |
| 48 hrs | 24.29 | 20.60 | 24.95 | 25.83 |
| 72 hrs | 21.57 | 21.72 | 24.03 | 21.39 |
| 96 hrs | 20.59 | 21.09 | 24.28 | 21.11 |
| 144 hrs | 18.18 | 19.52 | 22.94 | 20.01 |

The measurements of the inhibition zone were discontinued after 6 days. There was no inhibition of *Saccharomyces* growth in control samples of the film containing no antifungal agent. The results reveal that the antifungal agent embedded in the film is pharmacologically active and is able to inhibit the growth of *Saccharomyces cerevisiea* strain for a prolonged period of time.

Example 5

The formulations of the present invention were all prepared according to the general procedure which is described above (Preparation of Varnish).

| Ingredients | % w/w |
|---|---|
| Isopropyl Alcohol | 60.575 |
| Ethyl Acetate | 22.000 |
| Terbinafine HCl | 3.375 |
| Eudragit RS PO | 8.000 |
| Clobetasol Propionate | 0.050 |
| Propylene Glycol | 1.500 |
| Glycerol | 1.500 |
| Water | 1.500 |
| Urea | 1.000 |
| PEG 400 | 0.500 |
| Isopropyl Alcohol | qs to 100 |

Example 6

The formulations of the present invention were all prepared according to the general procedure which is described above (Preparation of Varnish).

| Ingredients | % w/w |
|---|---|
| Isopropyl Alcohol | 53.525 |
| Ethyl Acetate | 29.000 |
| Terbinafine HCL | 3.375 |
| Eudragit RS PO | 6.000 |
| Clobetasol Propionate | 0.050 |
| Glycerin | 4.220 |
| Water | 2.600 |
| Urea | 0.630 |
| PEG 400 | 0.6 |
| Isopropyl Alcohol | qs to 100 |

Example 7

The formulations of the present invention were all prepared according to the general procedure which is described above (Preparation of Varnish).

| Ingredients | % w/w |
|---|---|
| Ethyl Acetate | 29.2 |
| Acetone | 53.325 |
| Terbinafine HCL | 3.375 |
| Eudragit RS PO | 6.000 |
| Clobetasol Propionate | 0.050 |
| Glycerin | 4.220 |
| Water | 2.600 |
| Urea | 0.630 |
| PEG 400 | 0.600 |
| Acetone | qs to 100 |

Example 8

The formulations of the present invention were all prepared according to the general procedure which is described above (Preparation of Varnish).

| Ingredients | % w/w |
|---|---|
| Isopropyl Alcohol | 29.200 |
| Acetone | 53.700 |
| Terbinafine Base | 3.000 |
| Eudragit RS PO | 6.000 |
| Clobetasol Propionate | 0.050 |
| Glycerin | 4.220 |
| Water | 2.600 |
| Urea | 0.630 |
| PEG 400 | 0.600 |
| Acetone | qs to 100.000 |

Example 9

The formulations of the present invention were all prepared according to the general procedure which is described above (Preparation of Varnish).

| Ingredients | % w/v |
|---|---|
| Urea | 0.63 |
| PEG 400 | 0.60 |
| Clobetasol | 1.0 |
| Glycerin | 4.23 |

-continued

| Ingredients | % w/v |
| --- | --- |
| Eudragit RS PO | 6.0 |
| Water | 2.60 |
| Acetone:IPA (3:1) | To 100 ml |

Example 10

The formulations of the present invention were all prepared according to the general procedure which is described above (Preparation of Varnish).

| Ingredients | % w/v |
| --- | --- |
| Urea | 0.63 |
| PEG 400 | 0.36 |
| Clobetasol | 0.05 |
| Salicylic Acid | 2.5 |
| Glycerin | 4.23 |
| Eudragit L-100 | 6.0 |
| Water (0.1N HCl) | 2.60 |
| Acetone:IPA (3:1) | To 100 ml |

Examples of Using the Formulations

The compositions of the present invention may be applied to the infected nail and surrounding tissues once a day up to once a week.

It is understood that the precise concentrations and duration of treatment is a function of the tissue being treated. It is to be noted that concentrations may also vary with the age and condition of the individual treated. It is to be further understood that for any particular subject, the frequency of application should be adjusted over time according to the individual need and professional judgment of the physician or person administering or supervising the administration of the formulations.

It will be appreciated that the above descriptions are intended only to serve as examples, and that many other embodiments are possible within the spirit and the scope of the present invention.

The invention claimed is:

1. A sustained release therapeutic nail varnish for treating a human for a fungal infection, onychomycoses, psoriasis and/or chronic paronycia of the nail and/or surrounding tissue, comprising:
   a. a pharmaceutically effective amount of a pharmaceutical ingredient;
   b. about 0.3% to about 2% of a keratolytic agent;
   c. about 1% to about 15% of a humectant wherein the humectant is sorbitol, glycerol or a mixture thereof;
   d. water in an amount of about 0.1% to about 5% of the varnish solution;
   e. about 2% to about 15% of a hydrophobic methacrylic polymer; and
   f. a volatile solvent in an amount of about 60% to about 90%, relative to the total weight of the composition.

2. The sustained release therapeutic nail varnish of claim 1, wherein the pharmaceutical ingredient is an antifungal agent, an antipsoriatic agent, or a combination thereof.

3. The sustained release therapeutic nail varnish of claim 2, wherein the pharmaceutical ingredient is clobetasol.

4. The sustained release therapeutic nail varnish of claim 2, wherein the pharmaceutical ingredient is terbinafine.

5. The sustained release therapeutic nail varnish of claim 2, wherein the pharmaceutical ingredient is a combination of terbinafine and clobetasol.

6. The sustained release therapeutic nail varnish of claim 1, wherein the humectant is glycerol.

7. The sustained release therapeutic nail varnish of claim 1, wherein the keratolytic agent is urea.

8. The sustained release therapeutic nail varnish of claim 1, further comprising a plasticizer.

9. The nail varnish of claim 8, wherein said plasticizer is selected from the group consisting of dibutyl sebacate, diethyl phthalate, lanolin alcohols, mineral oil, petrolatum, polyethylene glycol, propylene glycol, triacetin, triethyl citrate, and mixtures thereof.

10. The sustained release therapeutic nail varnish of claim 2, wherein the pharmaceutical ingredient is an antipsoriatic agent present in an amount of about 0.02% to about 2%.

11. The sustained release therapeutic nail varnish of claim 1, wherein the volatile solvent is selected from the group consisting of an alcohol, a ketone, an ester, and mixtures thereof.

12. A sustained release therapeutic nail varnish for treating a human for a fungal infection, onychomycoses, psoriasis and/or chronic paronycia of the nail and/or surrounding tissue, comprising:
   a. a pharmaceutically effective amount of a pharmaceutical ingredient;
   b. a keratolytic agent in an amount of 0.3% to less than about 1% of the varnish solution;
   c. a humectant wherein the humectant is sorbitol, glycerol or a mixture thereof, and the humectant is present in a concentration of about 5% to about 35% (w/w), based on the weight of the non-volatile components;
   d. water in an amount of 0.5 to less than about 5% of the varnish solution;
   e. a hydrophobic methacrylic polymer in an amount of about 8% to about 35% based on the total weight of the non-volatile components; and
   f. a volatile solvent in an amount of about 60% to about 90%, relative to the total weight of the composition;
   wherein the weight ratio of polymer to the keratolytic agent is in the range from about 1:0.01 to about 1:1.

13. The sustained release therapeutic nail varnish of claim 12, wherein the pharmaceutical ingredient is an antifungal agent, an antipsoriatic agent, or a combination thereof.

14. The sustained release therapeutic nail varnish of claim 13, wherein the pharmaceutical ingredient is clobetasol.

15. The sustained release therapeutic nail varnish of claim 13, wherein the pharmaceutical ingredient is terbinafine.

16. The sustained release therapeutic nail varnish of claim 13, wherein the pharmaceutical ingredient is a combination of terbinafine and clobetasol.

17. The sustained release therapeutic nail varnish of claim 12, wherein the humectant is glycerol.

18. The sustained release therapeutic nail varnish of claim 12, wherein the keratolytic agent is urea.

19. The sustained release therapeutic nail varnish of claim 12, further comprising a plasticizer.

20. The nail varnish of claim 19, wherein said plasticizer is selected from the group consisting of dibutyl sebacate, diethyl phthalate, lanolin alcohols, mineral oil, petrolatum, polyethylene glycol, propylene glycol, triacetin, triethyl citrate, and mixtures thereof.

21. The sustained release therapeutic nail varnish of claim 12, wherein the pharmaceutical ingredient is an antipsoriatic agent present in an amount of about 0.02% to about 2%.

22. The sustained release therapeutic nail varnish of claim 12, wherein the volatile solvent is selected from the group consisting of an alcohol, a ketone, an ester, and mixtures thereof.

23. A method of treating a human for a fungal infection, onychomycoses, psoriasis and/or chronic paronycia of the nail and/or surrounding tissue, comprising topically applying to the surface of a nail, a nail varnish comprising:
   a. a pharmaceutically effective amount of a pharmaceutical ingredient;
   b. about 0.3% to about 2% of a keratolytic agent;
   c. about 1% to about 15% of a humectant wherein the humectant is sorbitol, glycerol or a mixture thereof;
   d. water in an amount of about 0.1% to about 5% of the varnish solution;
   e. about 2% to about 10% of a hydrophobic methacrylic polymer; and
   f. a volatile solvent in an amount of about 60% to about 90%, relative to the total weight of the composition.

24. The method of claim 23, wherein the pharmaceutical ingredient is clobetasol.

25. The method of claim 23, wherein the pharmaceutical ingredient is terbinafine.

26. The method of claim 23, wherein the pharmaceutical ingredient is a combination of terbinafine and clobetasol.

* * * * *